US006562209B1

(12) United States Patent
Sullivan et al.

(10) Patent No.: US 6,562,209 B1
(45) Date of Patent: May 13, 2003

(54) AUTOMATED COMPUTER CONTROLLED REPORTER DEVICE FOR CONDUCTING IMUNNOASSAY AND MOLECULAR BIOLOGY PROCEDURES

(75) Inventors: Brian M. Sullivan, Redondo Beach, CA (US); Denes L. Zsolnay, Rolling Hills, CA (US); Robert D. MacPhee, Jr., Long Beach, CA (US); Richard K. McHugh, Alhambra, CA (US)

(73) Assignee: Northrop Grumman Corporation, Redondo Beach, CA (US)

( * ) Notice: Subject to any disclaimer, the term of this patent is extended or adjusted under 35 U.S.C. 154(b) by 2 days.

(21) Appl. No.: 09/837,946

(22) Filed: Apr. 19, 2001

(51) Int. Cl.$^7$ ............................................. G01N 27/416
(52) U.S. Cl. ........................... 204/403.01; 204/403.14; 435/286.1; 435/817
(58) Field of Search ................ 204/403.01, 403.14; 435/817, 286.1, 287.1

(56) References Cited

U.S. PATENT DOCUMENTS

| 4,018,886 | A | | 4/1977 | Giaever | |
|---|---|---|---|---|---|
| 4,350,913 | A | | 9/1982 | Eddens | |
| 5,112,134 | A | * | 5/1992 | Chow et al. | 356/427 |
| 5,527,710 | A | | 6/1996 | Nacamulli et al. | |
| 6,100,045 | A | * | 8/2000 | Van Es | 204/403.14 |
| 6,108,607 | A | | 8/2000 | Kono et al. | |

FOREIGN PATENT DOCUMENTS

WO    WO 9907879    2/1999

OTHER PUBLICATIONS

Trau et al, Biosensors & Bioelectronics, 12 (6), pp. 499–510, 1997.*
Daniel C. Harris, "Quantitative Chemical Analysis", 5th Edition, pp. 93–97, 1998.*

* cited by examiner

*Primary Examiner*—Robert J. Warden, Sr.
*Assistant Examiner*—Kaj K. Olsen
(74) *Attorney, Agent, or Firm*—Ronald M. Goldman

(57) ABSTRACT

An electronic controller, such as a programmed microcontroller (33), controls a series of pumps (P1–P6) to automatically sequence the pumping of the individual fluids required by the ELISA procedure into a cell (or cells) necessary to produce a reporter, control the positioning of the carrier of the reporter (32, 35) adjacent the reporter sensor (28), analyze the data obtained from the reporter sensor and display (36) the concentration of the bioagent determined from the analysis of the foregoing data. The foregoing elements automate the ELISA procedure. Once started, the apparatus, governed by the program, conducts the test automatically without the necessity for human intervention. In accordance with a specific aspect, the foregoing components may be housed in a single package for easy portability; may be battery powered or line powered.

17 Claims, 4 Drawing Sheets

AUTOMATED COMPUTER CONTROLLED REPORTER DEVICE FOR CONDUCTING IMUNNOASSAY AND MOLECULAR BIOLOGY PROCEDURES

This application is related to U.S. application Ser. No. 09/105,538, filed Aug. 14, 1997 and U.S. application Ser. No. 09/105,539, filed Jun. 26, 1998, which are copending herewith.

FIELD OF THE INVENTION

This invention relates to quantitative in vitro detection and assaying of bioagents and nucleic acids, and, more particularly, to an automated apparatus for assaying of bioagents and nucleic acids on an industrialized scale.

BACKGROUND

It is known that the composition and relative quantities of reactants and products occurring in any chemical reaction, whether inorganic, organic or biochemical, must be determined while the reaction is in progress or at an equilibrium end point. Known procedures to perform such monitoring uses biologic or non-biologic molecules, here referred to as "recognition" molecules. Recognition molecules are capable of binding to either reactant or product molecules in a structure-restricted manner. That is, the recognition molecule binds to a specific three-dimensional structure of a molecule or to a two-dimensional surface that is electrically charged and/or hydrophobic in a specific surface pattern. Historically such molecules have been identified by exploring animal immune systems or through trial-and-error procedures. The foregoing analytic technique has in general been referred to as immunochemical, in reference to the selective recognition and binding capacity of immunoglobulins, even though substances other than antibodies may serve as recognition molecules.

Although applied in basic organic and biochemistry, the foregoing techniques have achieved the greatest development in clinical medicine. The most frequently used method is the enzyme linked immunosorbent assays ("ELISA"), which is applicable to a wide variety of fields, such as biotechnology, environmental protection and public health. In the immuno-chemistry field, enzyme immunoassays ("EIA") and, more particularly, ELISA are well known and important for detecting traces of foreign substances, such as antigens or antibodies in body fluids and tissues.

ELISA is a quantitative in vitro test for an antibody or antigen in which the test material is adsorbed on a surface and exposed to a complex of an enzyme linked to an antibody specific for the substance being tested for with a positive result indicated by a treatment yielding a color in proportion to the amount of antigen or antibody in the test material. The ELISA procedure is described more specifically, for one, in a book entitled Methods in Molecular Biology Vol 42, John R. Crowther, Humana Press, 1995. It should be recognized that the "antibody specific for the substance being tested for" in the foregoing definition constitutes a recognition molecule, earlier defined. It may also be recognized that ELISA-like approaches using other recognition molecules can also be used, such as aptamers, DNA, RNA & molecular imprint polymers.

More recently, the foregoing definition has been expanded beyond the colometric approach, wherein color is used as an indicia, to include yielding a rate of change of voltage or current conductivity in proportion to the amount of antigen or antibody in the test material, a voltametric or amperiometric approach to detection. Patent Cooperation Treaty application PCT/US98/16714, filed Aug. 12, 1998 (International Publication No. WO 99/07870), entitled "Electrochemical Reporter System for Detecting Analytical Immunoassay and Molecular Biology Procedures" (hereafter the "'16714 PCT application), claiming priority of U.S. patent applications No. 09/105,538 and 09/105,539"), describes both a colormetric and an electrochemical reporter system for detecting and quantifying enzymes and other bioagents in analytical and clinical applications.

The electrochemical reporter system of the 16714 PCT application employs a sensor for detecting the voltametric and/or amperiometric signals that are produced in proportion to the concentration of organic (or inorganic) reporter molecules, by redox recycling at the sensor. Although many different sensors are possible of application in the foregoing ELISA (and ELISA-like) methods, the preferred sensor in the foregoing method of the 16714 PCT application is stated to be of the kind described in a prior International Patent Application, published as PCT Publication No. WO 94/29708, published Dec. 22, 1994 (hereafter "IPN '708") in which a closely spaced (eg. nanometer scale spacing) interdigitated array ("IDA") of thin film noble metal microelectrodes are used. One set of the electrically conductive fingers in the interdigitated array serves as the cathode and the opposed set of electrically conductive fingers as the anode. The foregoing IDA is stated to be many times more sensitive than prior sensors due to redox recycling occurring at the surface of the electrodes.

With both an improved electrochemical ELISA protocol and an improved sensor the preferred ELISA system of the '16714 PCT application provides a more effective assaying system, one possessing greater sensitivity than prior assaying systems. The present invention also relates to detection and quantitative assaying by the electrochemical ELISA procedure. As brought out in the following description, the preferred embodiment of the present invention incorporates and improves upon the apparatus and method of the '16714 PCT application. Accordingly, the present application incorporates the content of each of the '16714 PCT application and the IPN '708 application here within as background to the present invention.

The electrochemical ELISA procedure and apparatus of the prior PCT application appears well suited to practice in a microbiology laboratory by highly skilled personnel who are alert to the details of the process. Other facilities or environments in which such an analysis is desirable, however, may not enjoy either the availability of highly skilled technicians or an adequately equipped laboratory. As example, one would like a simple and easily implemented test for the presence of the e-salmonella bacterium in meat products that could be conducted at meatpacking plants. In a military setting the field medics may need to quickly determine the presence of a deadly bioagent to which troops may have been or could become exposed. In such environments, the availability of a foolproof, user-friendly test apparatus that is able to analyze a sample and report a meaningful result with minimal human intervention is certainly desirable.

The system and apparatus of the present invention satisfies the foregoing need. As an advantage, the invention extends the benefit of the analytic procedures of the foregoing PCT applications to new fields and environments beneficial to the public.

Accordingly, a principal object of the present invention is to automate the ELISA procedure (and ELISA-like procedures), reducing the technical skills required to conduct the assay.

Another object of the invention is to provide apparatus for performing an ELISA of bioagents that is user friendly and capable of being performed by relatively unskilled personnel.

A further object of the invention is to make ELISA testing more portable, more easily accomplished, and of wider availability.

And a still further object of the invention is to computerize ELISA testing and make such testing available on an industrial scale.

SUMMARY OF THE INVENTION

In accordance with the foregoing objects and advantages, an electronic controller, such as a programmed microcontroller controls a series of pumps to automatically sequence the pumping of the individual fluids required by the ELISA procedure into a cell (or cells) necessary to produce a reporter, control the positioning of the carrier of the reporter adjacent the reporter sensor, analyze the data obtained from the reporter sensor and display the concentration of the bioagent determined from the analysis of the foregoing data. Once started, the apparatus, governed by the program, conducts the test automatically without the necessity for human intervention. In accordance with a specific aspect, the foregoing components may be housed in a single package for easy portability; may be battery powered or line powered.

An ancillary invention disclosed, that is incorporated within a preferred embodiment of the foregoing automated ELISA system, uses beads of magnetic material as a carrier for the antibodies that bind to a bioagent in the ELISA procedure enabling a magnetic field to position the carrier within the liquid contained in an examination cell of the ELISA system. A positionable magnet is included to produce the foregoing magnetic field.

The foregoing and additional objects and advantages of the invention, together with the structure characteristic thereof, where were only briefly summarized in the foregoing passages, will become more apparent to those skilled in the art upon reading the detailed description of a preferred embodiment of the invention, which follows in this specification, taken together with the illustrations thereof presented in the accompanying drawings.

DETAILED DESCRIPTION OF THE PREFERRED EMBODIMENTS

Figure 1:
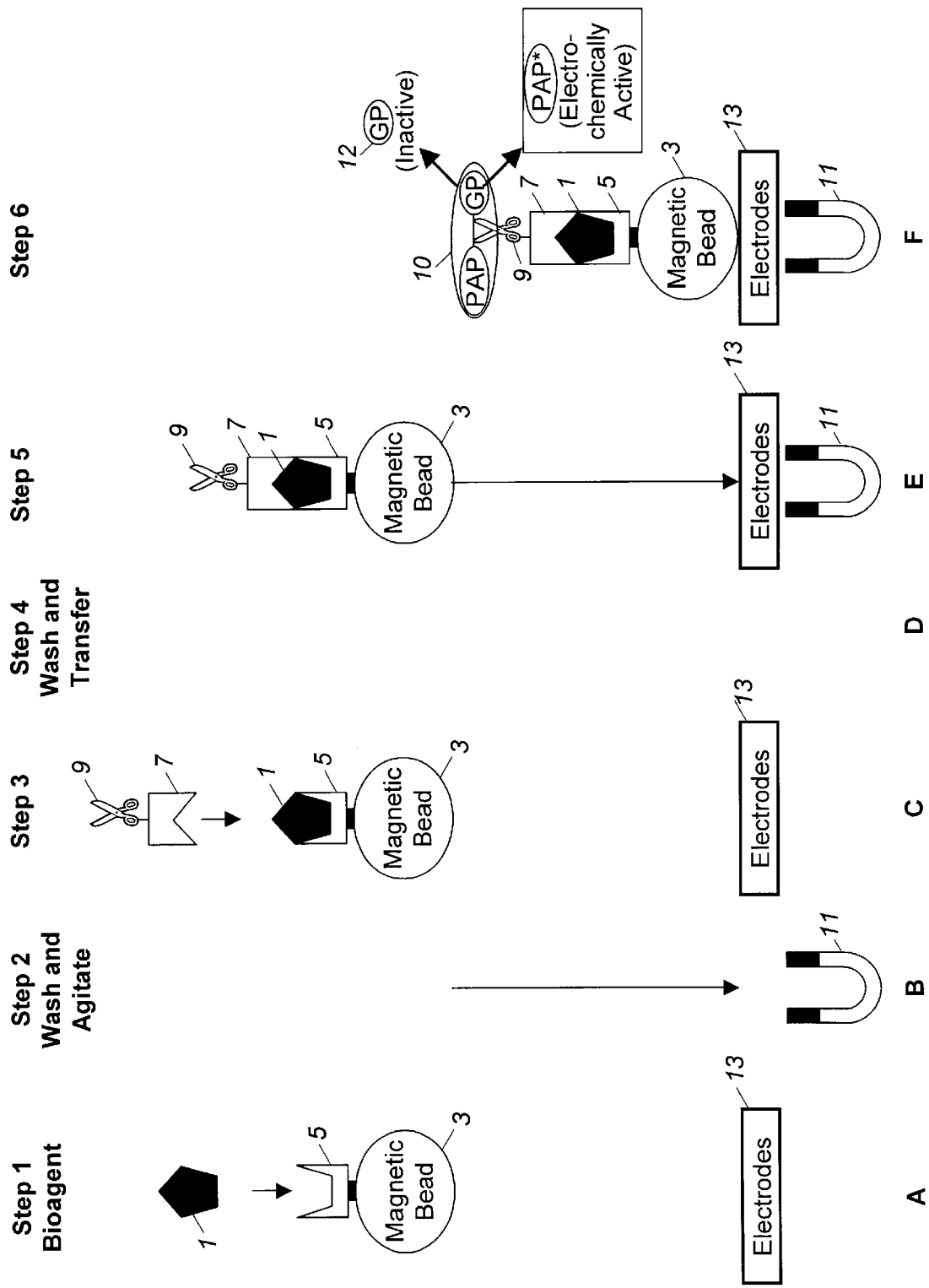
FIG. 1 is a pictorial illustration of the principal steps carried out by the principal embodiment of the invention.

Preliminary to the detailed description of the automated ELISA apparatus, it is believed that a general introduction to the steps processed by the apparatus and the biochemical basis underlying those steps should aid in understanding the invention. FIG. 1 to which reference is made pictorially illustrates the steps of the ELISA process that are incorporated within the embodiments of FIGS. 2 through 4, later described. In FIG. 1 STEPS 1 through 6 of the process are arranged in columns, left to right.

Initially in preparation for the testing, a sample solution is produced by placing the suspect material, the bioagent 1, represented by the pentagonal shaped symbol in a water-based buffer, such as a phosphate buffered saline solution. The foregoing sample solution is to be tested for the presence of a specific bioagent or may be one that is simply suspected of containing a certain bioagent. If desired, the suspect material may be preliminarily treated, such as by exposing the material to ultrasonic energy which breaks the material into multiple small clumps or even granules, which ensures maximum surface area exposure of the sample in solution.

In the first step, STEP 1, the foregoing sample solution 1 is placed into a container containing a quantity of particles whose surface is coated with an antibody 5 to the suspect bioagent, such as coated beads of magnetic material 3, and is mixed with those particles. The particular antibodies 1 that are used to coat the magnetic beads are known to bind to the bioagents of interest or of concern. That is, the antibody coating exhibits a chemical "stickiness" that is selective to specific bioagents. Despite such molecular stickiness, the solution prevents the beads from binding together or forming into clumps.

Because of the magnetic character of the beads, the beads can be manipulated by a magnetic field. The foregoing technique of using coated magnetic beads as a carrier is described in a patent to Glaever, U.S. Pat. No. 4,018,866, granted Apr. 19, 1977. In the preferred embodiment the magnetic beads are approximately four and one-half microns in diameter and are formed of iron. Other bead sizes, larger or smaller in diameter, may be substituted if the alternate size beads are found to accomplish the same result or otherwise produce satisfactory result in the test procedure. In lieu of beads other particles can be used if they are capable of being manipulated in the manner described herein.

Antibody 5 is a primary antibody or "1° Ab." Any bioagent that is present in the solution binds to a respective antibody 5 and thereby becomes attached to a respective one of the magnetic beads in the mixture-solution. The foregoing bond between the antibodies is recognized as a non-covalent bond. As becomes apparent, if no bioagent is present in the sample solution or if the bioagent that is present in the solution is not one that binds to the selected antibody 5, then nothing binds to antibody 5. The results obtained from further processing as described herein will then show nothing. For purposes of the description of operation, the sample solution being tested is presumed to carry bioagent 1, the analyte.

Thus, bioagent 1 bonds to antibody 5, as represented in STEP 3 by the seating of the pentagonal shaped bioagent symbol inside the mating cavity of the antibody symbol. Following STEP 1 the solution contains a quantity of bioagent molecules 1 bound respectively to a like quantity of coated magnetic beads 3.

In STEP 2 the mixture in solution of STEP 1 is optionally washed before proceeding with step 3. A suitable wash solution, as example is phosphate-buffered saline. Variants of the foregoing wash solution may include additional components, such as bovine serum albumin or detergents. To wash the mixture in solution, a magnet 11 is placed along one side of the vessel holding the solution. The vessel is constructed of non-magnetic material to permit penetration by magnetic fields. The magnetic field of the magnet penetrates the walls of the vessel and draws the magnetic beads to the side closest to the magnet, leaving the solution at the other side of the vessel relatively free of the coated magnetic beads. The side of the solution in the vessel vacated by the beads is then aspirated to remove the solution, suitably using an aspirating tube, without removing the coated beads, and the removed solution is replaced with clean solution. The solution is then agitated to re-suspend the beads in the wash solution and is followed by re-application of the magnetic field to again trap the beads. The foregoing agitation is preferably accomplished by pumping fluid into and out of the reaction area of the vessel.

The foregoing washing procedure is repeated as many times as experience shows is necessary to adequately clean the solution. As those skilled in the art appreciate, other washing protocols may be substituted for that described using the magnet without departing from the invention, but the magnet approach is believed most convenient.

In the next step, STEP 3, a second antibody, more specifically, an antibody 7 and enzyme 9 linked combination is added to the mixture in solution. The second antibody is also one that is known to bind to the bioagent of interest and may be either be one that is monoclonal, e.g. one that binds to only one specific molecule, or polyclonal, e.g. a mixture of different antibodies each of which shares the characteristic of bonding to the target bioagent. The enzyme 9, illustrated by the scissors symbol, is covalently bound to the second antibody 7 and forms a complex that is referred to as a secondary antibody-enzyme conjugate or "2°Ab-enz". As known by those skilled in, the art, an enzyme is a "molecule scissors", a protein that catalyzes a biological reaction, a reaction that does not occur appreciably in the absence of the enzyme. Enzyme 9 is selected so as to allow the subsequent production of an electrochemically active reporter, described hereafter in succeeding steps of the process.

The 2°Ab-enz binds to the exposed surface of the immobilized bioagent to form an "antibody sandwich" with the bioagent forming the middle layer of the sandwich, such as is illustrated in the pictorial of STEP 5 to which brief reference is made. Returning to completion of STEP 3, the next step, STEP 4, is to wash the beads in a manner similar to, but not necessarily identical to that described in STEP 2. The purpose at this juncture is to wash away any 2°Ab-enz that is not bound to a bioagent. If one employs a separate reaction chamber (as appears in one of the following embodiments) and electrochemical cell instead of a single cell, following the foregoing washing the beads are transferred from such reaction chamber to the electrochemical cell prior to undertaking STEP 5.

In STEP 5, a magnet 11 is applied to the end of the vessel holding the described solution to produce a magnetic field that draws, such as is represented by the arrow in the illustration, the magnetic beads and the attached antibody sandwich, the 1° Ab/bioagent/2°Ab-enz complex, in the solution to the exposed surface of the redox recycling sensor, formed of interdigitated electrodes 13.

Next in STEP 6 the substrate 10 of the enzyme is added to the solution and the substrate is cleaved by enzyme 9 to produce an electrochemically active reporter. The substrate of the enzyme is any substance that reacts with an enzyme to modify the substrate. This is illustrated in STEP 6 in which a preferred embodiment of substrate 10, p-amino phenyl galactopyranoside, is denominated PAP-GP. The effect of the enzyme is to cut the PAP, a para-amino phenyl, the electrochemically active reporter, from the GP 12, an electrochemically inactive substance, galactopyranoside.

The magnetic field produced by magnet 11 concentrates the foregoing chemical reaction at the surface of the electrodes 13 of the sensor. The rate of production of the foregoing reporter (PAP) is proportional to the initial concentration of bioagent. The reporter reacts at the surface of electrochemical electrodes 13, producing an electrical current through the electrodes that varies with time and is proportional to the concentration of the bioagent. An analysis of the electric currents produced in the foregoing manner over an interval of time and comparison of the values of that current with existing laboratory standards of known bioagents allows quantification of the concentration of bioagent present in the initial sample. More specifically, a least-square linear regression analysis of the data generates the slope of the current, representing the rate of change of current over time. That slope is then compared with corresponding slopes that were previously obtained in measurements of standard concentrations of the bioagent. By selecting the closest match between the measured and reference slopes the amount of bioagent present in the initial sample is determined.

As those skilled in the art appreciate, the foregoing method (and apparatus) of FIG. 1 modifies the prior ELISA procedure, for one, by incorporating into the process small size coated particles that may be manipulated in position within a confined fluid by a non-contacting manipulator that is located external of the confined fluid. In the preferred embodiment those small size coated particles are magnetic beads and the non-contacting manipulator is a magnet. Application of a magnetic field to position the magnetic beads facilitates the aspirating process during the washing steps and, further, in concentrating the chemical cleaving reaction (eg. cleaving of the substrate) at the surface of the sensor. Considered separately, the foregoing enhancement increases the efficiency of the ELISA process (and ELISA-like processes). More significantly, the foregoing modification is a component that contributes to the automated apparatus for performing the ELISA sample analysis presented in the illustrations of FIGS. 2–4 and the description, which follows in this specification.

Should other means to manipulate coated particles without contacting those particles be discovered and developed, it should be appreciated that such means may be substituted in the processing apparatus for the magnet and coated magnetic beads without departing from the scope of the present invention. It is also emphasized that while the preferred embodiment of the invention makes use of a sensor that contains interdigitally arranged conductors as presented in the prior art, other types of sensors, although less desirable, may be substituted without departing from the scope of the invention.

Figure 2:
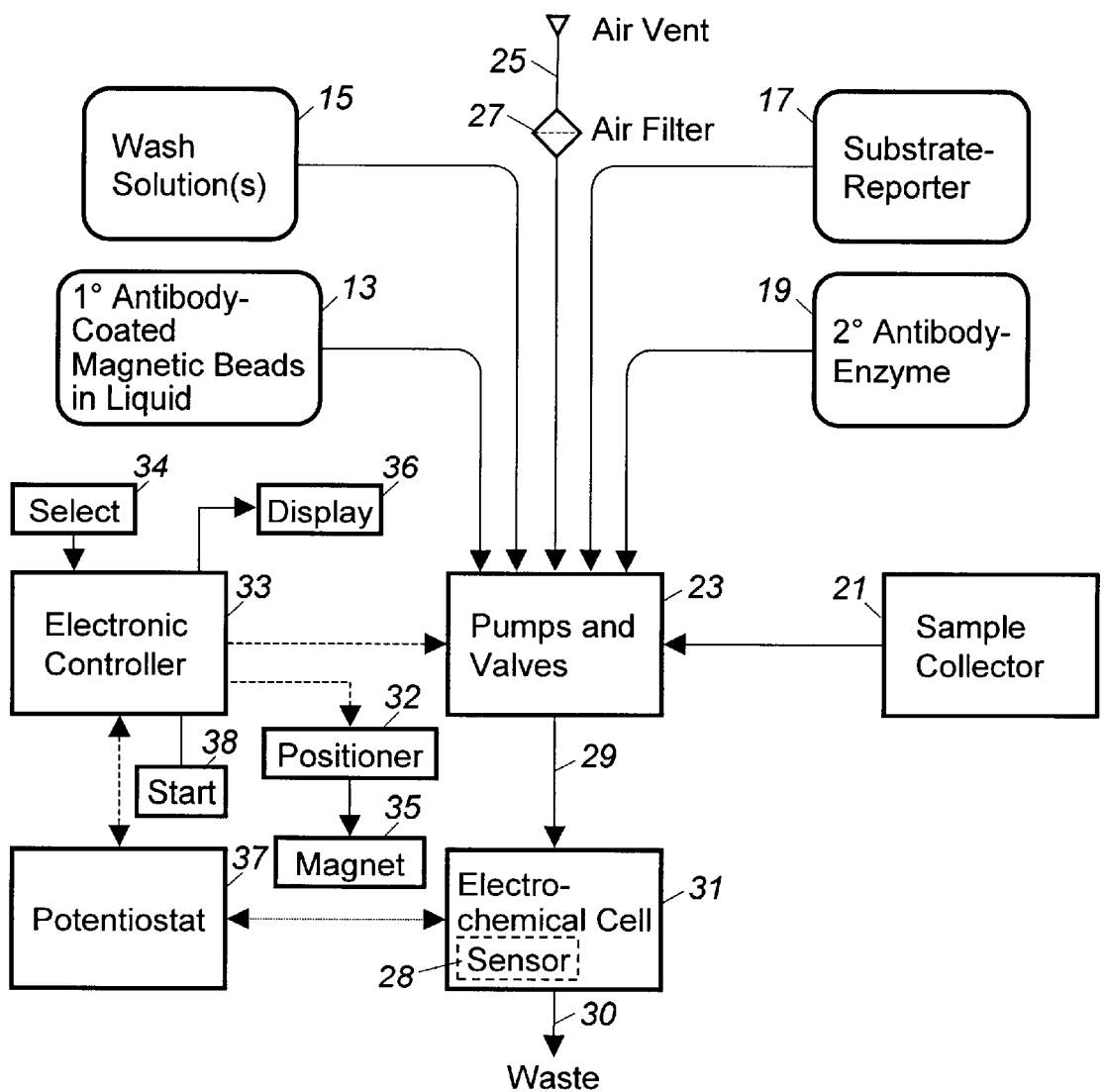
FIG. 2 is a block diagram of an embodiment of the invention.

Reference is next made to FIG. 2, which illustrates in block diagram form a first embodiment of the automated system, referred to as a single stage apparatus. The apparatus Includes four containers or, as variously termed, vessels 13, 15, 17 and 19, which hold, respectively, the 1° antibody coated magnetic beads in a liquid solution, the wash solution, the substrate reporter and the 2° antibody-enzyme solutions earlier described. The apparatus further includes a region in which to collect the sample that is to be analyzed, such as an inlet region or a vessel 21. Each of the foregoing vessels is connected by appropriate fluid conduits, the plumbing, to the pumps and valves unit 23 of the apparatus as illustrated.

Pump and valve unit 23 houses individual pumps, not separately illustrated in the figure, for each of the respective vessels. An air vent 25 and air filter 27 are also plumbed into the pumps and valves unit. The air vent and air filter provides a vent to allow air to separate from solutions and/or remove solutions from tubes. A fluid conduit 29 extends from the pumps and valves unit into electrochemical cell 31, the vessel in which the examination is made. Waste conduit 30 extends from cell 31 to an appropriate sump or sewer, not illustrated, to permit disposal of the waste of the process. The apparatus includes an electronic controller 33, which is a programmed microprocessor or microcontroller, a positioner 32, suitably a solenoid, a magnet 35 and a potentiostat 37, the latter of which is under control of the controller as represented by the dash lines. The potentiostat is electrically coupled to a current sensor 28, represented in dash lines, located inside cell 31. That current sensor is preferably formed of interdigitated electrodes, earlier described. Electronic controller 33 includes a selector 34 through which the operator may select the particular antigen for which the analysis of the sample is being undertaken, a start button 38 and a display 36, preferably a liquid crystal display ("LCD"), by which the assay may be reported to the operator.

Magnet 35 is a permanent magnet. The magnet is supported and positioned against examination cell 31, when required, by positioner 32. The positioner is a solenoid actuated electromechanical device that positions the magnet so that the magnetic field of the magnet is directed into the examination cell or away from that cell as required by electronic controller 33. Normally, positioner 32 directs the magnetic field of magnet 35 away from the examination cell, the default direction. When the positioner receives the command from and is energized by the electronic controller, the positioner moves the permanent magnet into position adjacent the cell so that the permanent magnet directs the magnetic field into the examination cell and through the electrodes of the sensor inside that cell. When a command is received from controller 33 to extinguish the magnetic field in examination cell 31, the positioner moves the permanent magnet away.

As those skilled in the art appreciate, an electromagnet may be substituted for the permanent magnet and permanently positioned in place adjacent to and facing the examination cell. In that event, the controller would supply energization current to the electromagnet when a magnetic field is required during the process. However, because an electromagnet requires much more electrical power than the permanent magnet arrangement, the permanent magnet arrangement is preferred to enhance portability of the apparatus.

Potentiostat 37 supplies the voltage to the electrode array, the sensor 28, that monitors the reporter, described in step 4 of FIG. 1, earlier described disposed on the bottom or side of electrochemical cell 31. That is, the sensor carries any extra electrical current that flows in series through the electrode array and potentiostat as a result of the "redox recycling" reaction that takes place during the latter stage of analysis when the enzyme substrate is cleaved to release the reporter (Step 6 earlier described in FIG. 1). The potentiostat is also coupled to an input of the controller 33 and communicates the electrical current levels that flow through the interdigital array to the controller.

Electronic controller 33 is a programmed microprocessor, microcontroller, computer, as may be variously termed, or the like. The electronic controller controls each of the pumps and valves housed in unit 23 and controls energization of magnet positioner 32. The controller also enables and receives monitored current readings from potentiostat 37. Controllers of the foregoing type are quite small in size and may be housed or embedded in the structure of one of the units, such as in pumps and valves unit 23 so as to be inconspicuous. The foregoing components may all be packaged into a small size compact unit that may easily be carried by an individual. For added portability, the controller and pumps may be battery operated. Otherwise the apparatus may be supplied with electrical operating power from the facility in which used or by a motor generator set.

Electronic controller 33 includes a memory, not separately illustrated, such as ROM or EPROM to permanently store the operating system and the programs as well as temporary memory such as RAM, not separately illustrated. The principal programs of the controller are evident from the description of operation that follows. It will be realized that the controller serves as a sequencing device for controlling the pumps, as a collection point for data, and as a calculating machine for analyzing the data and displaying the result.

The electrochemical reaction sensor employed in the apparatus of FIG. 2 may be any type of sensor that supplies information on the reporter and supplies that information to the electronic controller. One such sensor applies a given voltage across at least two spaced electrodes disposed in the electrochemical cell and senses the level of electric current that flows between those electrodes. However the preferred sensor is of the interdigitated array type one that is described in the cited '16714 PCT application, IPN '870" application and publications cited in the background to this invention. The interdigitated array structure is promulgated as being the most sensitive and, hence, allows better resolution of the data than other known sensors to date in this application.

For operation, electrical power is connected to electronic controller 33. The operator determines the particular bioagent that is being sought in the sample material, preferably prepares the sample in accordance with the ultrasonic energy exposure earlier described, places the sample in a solution in sample collector 21, and selects the particular bioagent on selector 34. Vessels 13, 15, 17 and 19 are filled with the appropriate ingredients, earlier described and not here repeated. The operator operates the start button 38 and in response electronic controller 33 commences the automatic operation specified in the stored program.

The program of the controller motivates dispensing the contents of sample collector 21 into cell 31 by commanding the controller to briefly energize an electrical pump associated with the sample collector. The energized pump pumps the sample-in-liquid through the plumbing, including conduit 29, and into cell 31, which may be referred to as the examination cell. Concurrently or subsequently the program motivates dispensing of the contents of vessel 13, the 1°antibody coated magnetic beads in liquid, by commanding the controller to energize a second electric pump associated with that vessel for a short interval. The second electric pump pumps the 1°antibody coated magnetic beads-in-liquid into examination cell 31. Presuming the suspect bioagent is present in the sample material previously deposited in the cell, the bioagent binds to the antibody coating on the magnetic beads, as earlier described in STEP 1 of FIG. 1.

Although the description of the embodiment refers to individual pumps to accomplish the prescribed pumping, those skilled in the art recognize that other less expensive arrangements may be employed in alternative embodiments that accomplish the pumping with a configuration of electrically controlled valves and pumps that allows pumping of fluid from specific vessels as selected by the controller. As example, a valve could be associated with each vessel, the controller would select the particular valve to open, and then cause a pump to operate and draw the fluid through the valve.

Returning to the operation, following a short interval the controller program next commands the washing of the ingredients in the fluid in cell 31. For the washing operation, the program commands energization of magnet positioner 32, which moves permanent magnet 35 into position to orient a magnetic field extending inside of examination cell 31, and commands energization of a third pump, not illustrated in the figure, referred to herein as the aspirating pump. The magnetic field draws the magnetic beads (and the biochemicals bound thereto) to one side of the cell, vacating the beads from the solution on the other side of the cell. The aspirating pump connects to a conduit that extends into the vacated side of the solution, and the third pump aspirates the fluid and expresses the waste fluid through waste conduit 30. After a suitable interval the program halts the third pump and energizes a fourth pump that connects to a second vessel in wash solution 15 and pumps sufficient clean fluid to replace the fluid that was removed, completing the wash. The foregoing wash function corresponds to STEP 2 of FIG. 1. The solution is then agitated to re-suspend the beads in the solution as by aspirating a small amount of fluid from the vessel and then repumping the aspirated fluid back into the vessel often referred to as an "up-down" of the solution.

The foregoing washing procedure may be repeated the number of times required by the controller program, and the number written into the program is one that satisfies the requirements of a particular operator's experience. For purposes of this description, the washing step is performed once.

The program then motivates the delivery of the 2°antibody-enzyme into examination cell 31 by energizing the pump associated with vessel 19 for a predetermined interval. In the examination cell, the antibody-enzymes then bind to another region of the bioagent, producing the 1°Ab/bioagent/2°Ab-enz complex. The latter is the same as described in STEP 3 of FIG. 1.

Magnet 35 remains set in the position previously described. At this stage the controller program does not command positioner 32 to restore the orientation of magnet 35 to the default position, since the magnetic field is used again in a subsequent operation. The magnetic field produced by magnet 35 draws the magnetic beads 3 and the ingredients carried on the beads toward the sensor 28. This is the same as represented in STEP 5 of FIG. 1. In alternate embodiments of the apparatus, the program may be modified to require the magnet to reorient the magnetic field away from examination cell 31; and then, later in the process when the magnetic field is again required, command positioner 32 to reorient the magnet so as to again position the magnetic field into the examination cell. The foregoing alternative is seen as an equivalent to the described program, but is less preferred as the extra steps appear unnecessary.

The program of controller 33 next motivates the delivery of the substrate reporter in vessel 17 into the solution in examination cell 31 by commanding energization of an electric pump, not illustrated in the figure, associated with vessel 17. The pump is energized for a predetermined interval and pumps the substrate into the contents within examination cell 31. Cleavage of the substrate by the enzyme commences.

As recalled from the preceding paragraphs, magnet 35 produces a magnetic field that extends through the non-magnetic walls of electrochemical cell 31 and draws the magnetic bead complex to the surface of the test electrodes of the electrochemical sensor, not illustrated, disposed inside cell 31. At that location adjacent the electrode surface of the sensor, the bound enzymes cleave the substrate to produce the reporter molecules.

Sensor 28 monitors the reaction and reports to the electronic controller 33. In turn, the controller program analyzes the data obtained. To monitor electric current through the examination cell the potentiostat applies a voltage across the spaced interdigitated electrodes, earlier described, which serve as sensor 28. That applied voltage produces an electrical current that passes from one spaced electrode, the anode, through the solution to the other electrode, the cathode. Absent a reaction in the solution, the electric current attains a certain default or base value, depending upon the resistivity of the solution. As the reaction commences to produce the reporter, the resistivity of the solution decreases, increasing the current. The effect is referred to by electrochemists as redox recycling. As the reaction continues producing greater numbers of reporter molecules, the resistivity changes further, as does the electric current. The rate of change of the current is a measure of the concentration of the selected bioagent. Information of the current, whether the information is in digital form or analog form, is coupled to electronic controller 33, which analyzes the changing data in real time.

Essentially concurrently with the pumping of vessel 17, the controller program commences the checking and assembling of the data on electrical current flow through the sensor by repetitively checking the current readings supplied by potentiostat 37 over a predefined interval of time. As example, one hundred readings may be taken equally spaced over an interval of ten minutes. The data obtained is temporarily stored in the memory of the electronic controller. The program then performs a least-square linear regression analysis of the data and the analysis generates the slope of the sensor current (eg. change of current level vs. time), a number that represents the rate of change of current.

The electronic controller also stores in memory (ROM or EPROM) a library of the standards that have previously been established in the laboratory to identify bioagents or antigens and the concentration of the respective antigen in a solution by measuring the rate of change of current that occurs when using the known electrochemical ELISA procedure. Each antigen or bioagent produces a rate of change of current that depends on the concentration of the bioagent in the sample. For any given combination of recognition molecule(s) and bioagent or other antigen, a given concentration produces a unique rate of change of current. The increase in current as a function of time from the beginning of the chemical reaction to produce the reporter is essentially linear, and produces a straight line curve of the type $I=at+b$, where "t" represents time, "b" is an initial constant, a number, and "a" is the slope of the line, also a number. The foregoing slope information and the correlation of that information to respective concentration levels has been tabulated and serves as the standards.

Thus, for each combination of recognition molecule(s) and bioagent or other antigen that is to be studied, the library, often referred to as a "look-up table", contains the correlation between the slope numbers and the concentration levels correlated to those slope numbers. After concluding the regression analysis and obtaining the slope number, the controller program checks to determine which bioagent or antigen was selected by the operator and then accesses the stored look-up table for the selected bioagent or antigen. The computer then compares the slope obtained in the foregoing regression analysis with corresponding slopes obtained in measurements of standard concentrations. Once the computer locates the closest match, the computer then displays the concentration of the antigen on display 36. Optionally, the computer may be programmed to also display the calculated slope. Further, since the volume of the electrochemical cell is known, the computer may also optionally display the total quantity of antigen in the test sample.

The foregoing apparatus is recognized as being automatic in operation, is very "user-friendly" and does not require highly skilled personnel to operate. Incorporated within a compact housing and with optional battery or house supply power the apparatus is portable and suited for use on location.

Figure 3:
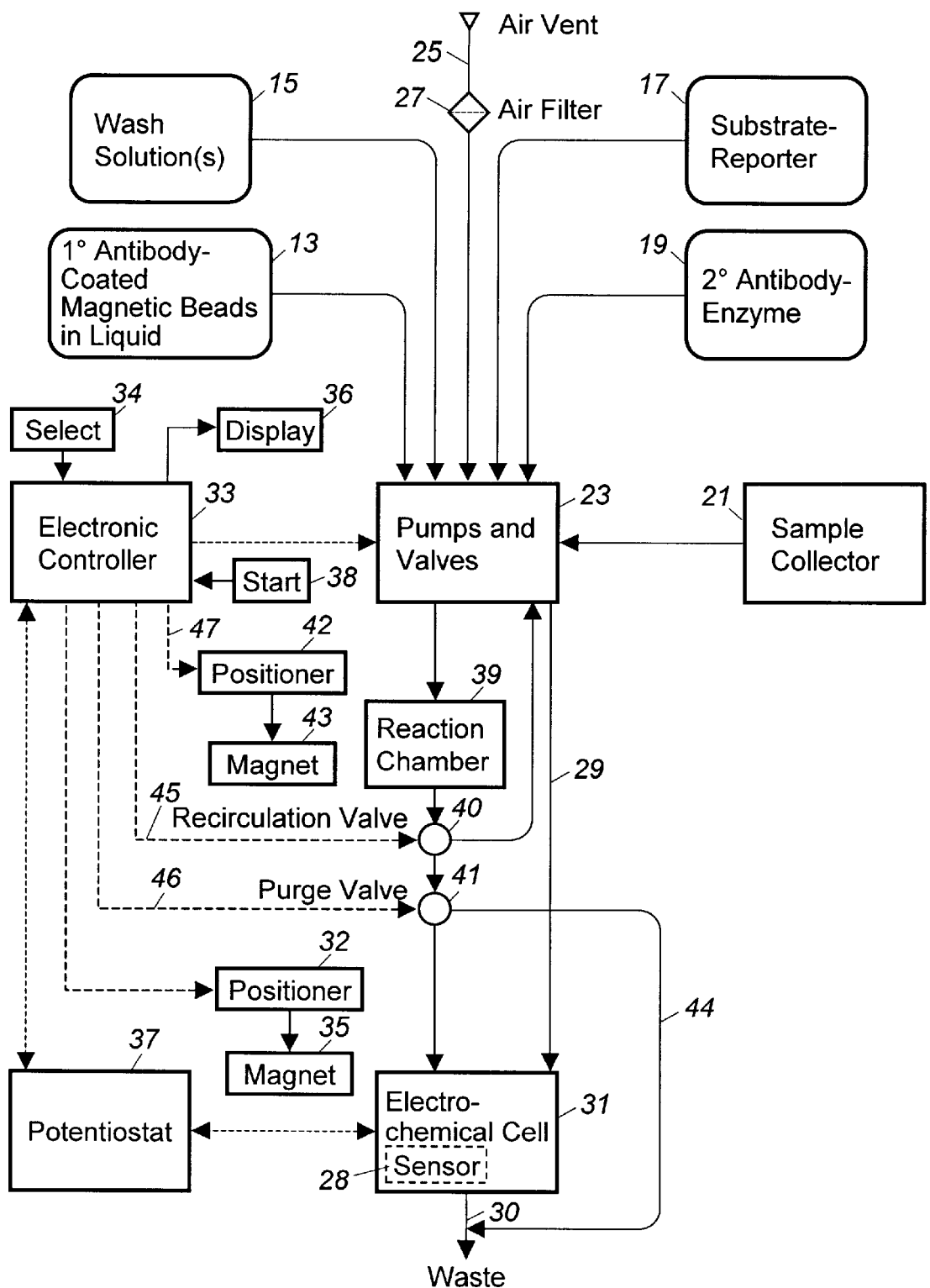
FIG. 3 is a block diagram of a second embodiment of the invention.

Reference is made to FIG. 3 that shows a block diagram of an alternative embodiment of the apparatus. This second embodiment is regarded as a two stage apparatus, whereas the apparatus of FIG. 1 is regarded as a single stage apparatus. For convenience, the components of the embodiment of FIG. 2 that are essentially the same in structure as those previously described in FIG. 1 are given an identical denomination. Those components that are changed slightly are denominated by the same number used for the corresponding element and the numbers are primed.

As inspection of FIG. 3 shows that many of the functional elements of this embodiment are the same as in the prior embodiment. The components that have been added include a separate reaction cell or chamber 39, recirculation valve 40, purge valve 41, an additional magnet 43 and associated positioner 42 for the magnet, some additional fluid conduits, some additional. outputs and control lines from the electronic controller, and a slightly changed program for the electronic controller to accommodate the additional components and functions.

In this embodiment the reactions and washes are carried out in a separate vessel, the reaction chamber 39. Of necessity, a separate magnet positioner 42 and magnet 43 are employed in connection with the nonmagnetic chamber. The plumbing and pump arrangement also differs. The electronic controller is programmed to handle the functions that correspond to steps 1–6 of FIG. 1 and all of the same operation as in the embodiment of FIG. 2, excepting the cleavage operation that generates the reporter. In the foregoing positioner 42 and magnet 43 are used the same as that described for positioner 32 and magnet 35 in the embodiment of FIG. 2.

At the reporting stage in the present embodiment, the controller opens valves 40 and 41 permitting the magnetic beads in solution to transfer into examination cell 31, and commands positioner 32 to position magnet 35 to direct the magnetic field into cell 31 and through the sensor 28. The controller then directs the final chemical substrate 17 to be pumped via conduit 29 into the examination cell 31. As in the prior embodiment, electronic controller 33' senses the electrical current through the sensor and potentiostat 37, which is changing, determines the rate of change of current, eg. the slope, and from that slope determines the concentration of the bioagent. The controller then displays the concentration on display 36. Upon conclusion of the examination the contents of the cell are expressed through conduit 30 as waste.

The embodiment of FIG. 3 includes some additional features. Valve 40 is referred to as a recirculation valve. Should the program call for recirculating the solution, the controller sets valve 40 to open a path into a circular conduit. An aspirating pump, not illustrated, located within unit 23 pumps the solution to mix the solution.

Valve 41 is referred to as the purge valve. Instead of commanding that the solution in chamber 39 be pumped into cell 31, the controller may instead set valves 40 and 41 to open a passage into conduit 44 and then initiate an electric pump that pumps the solution in chamber 39 through the valves and out conduit 44. Conduit 44 leads into conduit 30 and leads to the waste disposal system.

Figure 4:
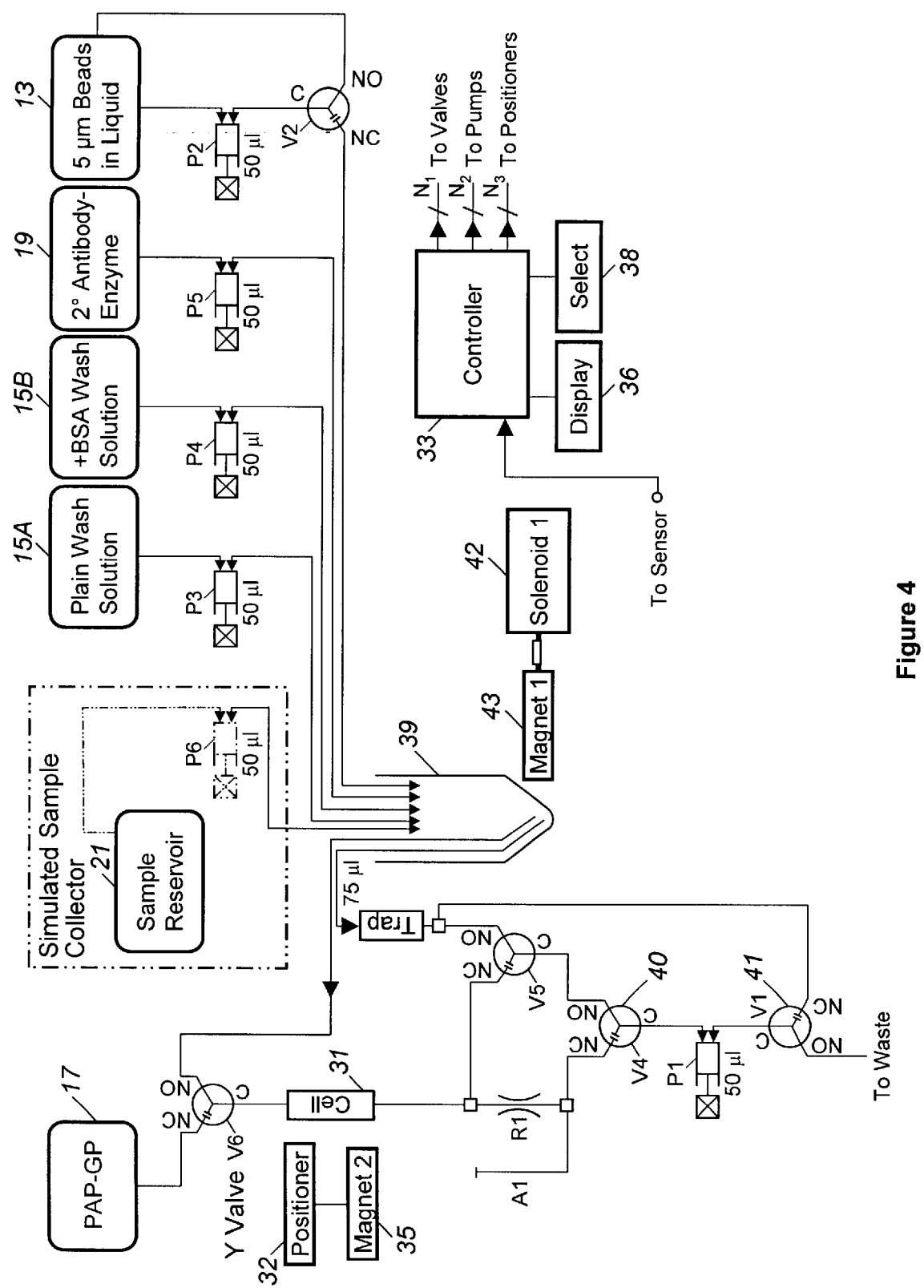
FIG. 4 is a partial schematic diagram of a third embodiment of the invention that improves upon the embodiment of FIG. 3.

Reference is next made to the schematic illustration of FIG. 4, which illustrates another embodiment of the invention, a variation of the embodiment of FIG. 3, earlier described. For convenience, the denomination of the components in this embodiment, which are the same as those used in the embodiment of FIG. 3, are identified by the same number, with few exceptions. The embodiment of FIG. 4 contains electrically operated pumps P1, P2, P3, P4, P5 and P6 and a series of electrically operated valves, V2, V1, V4, V5 and V6, all of which are controlled by the controller 33. The convention adopted to describe the condition of a valve when referring to same as either open or closed may be stated briefly. When a valve outlet (or inlet) is referred to as being "closed", the term means that the outlet is blocked so that fluid cannot flow there through. When the valve outlet (or inlet) is said to be open, the term means that the outlet (or inlet) is unobstructed, and fluid is able to flow there through. Each of the foregoing valves is a two-way valve and contains an inlet and a pair of outlets, one of the outlets being normally closed, as illustrated by a gap, and the other of which is normally open, as represented by an unbroken line. When the valve is energized, the foregoing state of the outlets reverses.

Controller 33, display 36 and start switch 38 are illustrated in block form. The controller outputs to the respective valves, pumps and positioners are represented by cable outputs N1, N2 and N3, in which the cable contains the requisite number of electrical leads, N, for the respective components associated with the cable. To avoid undue complication to the schematic, the electrical leads are not extended to the respective controlled component in as much as those skilled in the art will understand the connections. Likewise the input lead from the sensor, not illustrated, disposed in examination cell 31, is only partially illustrated.

Pump P2 is associated with vessel 13 and is for pumping the (5 micrometer) magnetic beads in liquid solution contained in the vessel through the valve V2 and, when the valve is energized, the plumbing lines into reaction cell 39. Valve V2 is a two-way valve. The valve contains a normally closed passage that leads into a conduit that in turn terminates in vessel 13, forming a recirculating fluid loop in the system. Thus, when pump P2 is energized by the controller, and valve V2 remains deenergized, such as illustrated in the figure, the magnetic bead solution is pumped through the recirculating loop. The recirculation of the magnetic bead solution helps to homogenize the distribution of the beads in the solution. When both pump P2 and valve V2 are energized, the valve opens the recirculating loop and closes the passage through the conduit into reaction cell 39.

Pumps P3 and P4 are associated with vessels 15A and 15B. The two vessels contain different wash solutions, as example, phosphate buffered saline solution in 15A and Bovine Serum Albumin ("BSA"), respectively. The BSA is a main component of cow blood in water, a random protein that prevents the magnetic beads from competing for binding sites. Thus instead of a single wash in this embodiment, a double wash with different washing solutions is accomplished. When commanded by the controller, pumps P3 and P4 will respectively pump the contents of vessels 15A and 15b through respective conduits into reaction cell 39.

Pump P5 is associated with vessel 19 containing the 2° antibody-enzyme and pumps the contents into the foregoing cell via a separate conduit into the reaction cell. Pump P6 is associated with vessel 21 in which the sample of bioagent is placed in liquid solution. The pump pumps the sample solution through a separate conduit into the reaction chamber.

The enzyme substrate (PAP-GP) is contained in vessel 17. Valve V6 contains a normally closed inlet, a normally open inlet and an outlet. The normally open inlet connects via a conduit to vessel 17 and opens in the bottom side of that vessel. The normally closed inlet connects via a conduit to an aspiration tube that is disposed in reaction cell 39. The outlet of the valve connects through a conduit to the upper end of the examination cell 31. The examination cell contains an outlet at the bottom end of the cell that connects via a conduit to a normally open inlet of Valve V4 and to a standpipe A1 that opens to the atmosphere. The foregoing conduit also includes a flow restrictor R1.

Each of valves V4 and V5 contain a normally open inlet and a normally closed inlet and an outlet. Valve V1 contains an inlet, a normally closed outlet and a normally open outlet. Pump P1 is connected by conduit in series between the outlet of valve V4 and the inlet of valve V1. The normally open outlet of valve V4 connects to the outlet of valve V5 and the normally open inlet of valve V5 connects via a trap and conduit to a second aspiration tube that extends into the reaction cell 39.

Assuming that the stage of operation of the foregoing system is ready to examine for the bioagent in examination cell 31, the solution located in examination cell 39 must be transferred into the examination cell 31 and the enzyme substrate (PAP-GP) must be added thereto. The transfer is accomplished by aspirating the solution from the examination cell by operating pump P1 and valve V4. In operating pump P1 creates an aspirating force inside cell 31 through the now closed inlet of valve V4 and the conduit into expelling gas and/or fluid through the inlet and normally open outlet of valve V1. The short closed fluid tube A1, referred to as an accumulator, is also connected in common with the normally closed passage in valve V4. The accumulator is filled with air and serves as an "air spring" that evens out the flow rate of the solution to a uniform slow fluid motion. The draw pulls solution from reaction cell 39 via the aspirating tube, the normally open inlet of Valve V6 and the outlet of that valve and into cell 31. The amount of time required to pump and adequately fill the examination cell is pre-calibrated during the design of the system and is known to the program in the controller.

When the foregoing transfer is completed, the controller then additionally energizes valve V6. With energization, the normally closed valve inlet of Valve V6 is switched to open (and vice-versa for the normally open valve inlet). Pump P1 aspirates a portion of the contents of cell 31 containing the sample while drawing the PAP-GP from vessel 17 through valve V6 and into cell 31.

The foregoing system operates essentially the same as previously described for the preceding embodiment. Prior to operating valve V6, the controller readies the examination cell for detection of the redox recycling that is expected to occur. Thus, controller 33 commands positioner 32 to energize and the positioner in turn places the magnet in the proper orientation to have the magnetic field penetrate the non-magnetic walls of examination cell 31 and pass through the electrochemical sensor, not illustrated in the figure, inside the cell. When the PAP-GP is subsequently introduced into cell 31, the sensor will monitor the current levels over a period of time, reporting the current levels to electronic controller 33. As in the prior embodiments, the controller determines the concentration of the bioagent and displays the result on display 36.

Valve V4 is used to determine the flow speed of fluid through cell 31 by interposing a restrictor R1 and parallel accumulator A1. High flow rates are desirable for flushing the cell after a test. Low rates are better when introducing the coated magnetic beads so that they are not swept past the magnet by the force of the flow.

As one appreciates, the foregoing describes specific aspects of the mechanization of the ELISA process. The embodiment of FIG. 4 automatically carries out the same functions as earlier described for FIGS. 1, 2 and 3 in automatically accomplishing the ELISA process, which need not be repeated.

The means for holding the sample solution in the prior embodiments was referred to as a vessel. It should be understood that the term vessel in that connection is intended to refer to any region, pipe, conduit or any other suitable means for holding the sample consistent with the described operation, and is to be not limited in meaning to a jar or container and may be referred to as a sample holding means.

It is believed that the foregoing description of the preferred embodiments of the invention is sufficient in detail to enable one skilled in the art to make and use the invention without undue experimentation. However, it is expressly understood that the detail of the elements comprising the embodiment presented for the foregoing purpose is not intended to limit the scope of the invention in any way, in as much as equivalents to those elements and other modifications thereof, all of which come within the scope of the invention, will become apparent to those skilled in the art upon reading this specification. Thus, the invention is to be broadly construed within the full scope of the appended claims.

What is claimed is:

1. Apparatus for conducting an electrochemical enzyme linked immunosorbent assay (ELISA) for a bioagent, protein or nucleic acid comprising;
   a plurality of vessels, said plurality of vessels including:
   a first vessel containing 1° antibody coated magnetic beads in liquid;
   a second vessel containing a wash solution;
   a third vessel containing a 2° antibody linked enzyme;
   a fourth vessel containing a substrate reporter; and
   sample holding means containing a sample solution containing said bioagent, protein or nucleic acid;
   an examination cell;
   an electronic controller, said electronic controller including a program, a start switch and a display;
   a sensor for electrically detecting the level of reporter present in said examination cell and supplying said detected level of reporter present to said electronic controller;
   said electronic controller for motivating passage of the respective contents of each of said vessels into said examination cell when required by said program and for motivating removal of the contents of said examination cell in whole or in part when required by said program;
   said program configured for performing an ELISA technique, wherein motivation of the contents of each of said vessels is motivated in a sequence;

said program including means for motivating the contents of said fourth vessel into said examination cell and initiating collection of the detected level of reporter present at said sensor at each of a plurality of time intervals following motivation of the contents of said fourth vessel into said examination cell; whereby insertion of the contents of said fourth vessel into said examination cell when said respective bioagent, protein or nucleic acid is present in said examination cell produces an electrochemical redox recycling reaction inside said examination cell to produce levels of reporter that increases with time;

said program further including an analysis program for analyzing the detected level of reporter at each of said plurality of time intervals and determining the concentration of bioagent, protein or nucleic acid present in said sample when said respective bioagent, protein or nucleic acid is present in said sample and displaying said concentration on said display.

2. The apparatus for conducting an electrochemical ELISA for a bioagent, protein or nucleic acid comprising as defined in claim 1, wherein said electronic controller includes a look-up table, said look-up table containing a plurality of numbers defining slopes of lines representing detected levels of reporter versus time and a plurality of bioagent concentrations with each of said plurality of bioagent concentrations being associated with a respective one of said plurality of numbers, wherein for each slope represented in said look-up table, a concentration of said respective bioagent, protein or nucleic acid may be determined;

wherein said analysis program further comprises:

a regression analysis program for performing a least-square linear regression analysis on said detected level of reporter taken at each of said plurality of time intervals to determine a number, said number defining a slope of a line representing detected levels of reporter versus time:

a look-up program for looking up said number determined by said regression analysis program in said look-up table and locating the corresponding concentration of said bioagent represented thereby.

3. The apparatus for conducting an electrochemical ELISA for a bioagent, protein or nucleic acid as defined in claim 1, further comprising:

a plurality of electric pumps, each pump being associated with a respective one of said first through fourth vessels and said sample holding means for conveying contents from the respective vessels into said examination cell when said pump is energized;

said electronic controller being coupled to said plurality of pumps for controlling the energization of said pumps in accordance with said controller program.

4. The apparatus for conducting an electrochemical ELISA for a bioagent, protein or nucleic acid as defined in claim 1, further comprising: an aspirating pump, said aspirating pump for pumping contents from said examination cell when energized by said electronic controller.

5. Apparatus for conducting an electrochemical enzyme linked immunosorbent assay (ELISA) for a bioagent, protein or nucleic acid comprising:

a plurality of vessels, said plurality of vessels including:

a first vessel containing 1° antibody coated magnetic beads in liquid;

a second vessel containing a wash solution;

a third vessel containing a 2° antibody linked enzyme;

a fourth vessel containing a substrate reporter; and sample holding means containing a sample solution containing said bioagent, protein or nucleic acid;

an examination cell;

an electronic controller, said electronic controller including a program, a start switch and a display;

a sensor for electrically detecting the level of reporter present in said examination call and supplying said detected level of reporter present to said electronic controller;

said electronic controller for motivating passage of the respective contents of each of said vessels into said examination cell when required by said program and for motivating removal of the contents of said examination cell in whole or in part when required by said program;

said program configured for performing an ELISA technique, wherein motivation of the contents of each of said vessels is motivated in a sequence to pass the contents of the respective vessels into said examination cell;

said program including means for motivating the contents of said fourth vessel into said examination cell and initiating collection of the detected level of reporter present at said sensor at each of a plurality of time intervals following motivation of the contents of said fourth vessel into said examination cell; whereby insertion of the contents of said fourth vessel into said examination cell when said respective bioagent, protein or nucleic acid is present in said examination cell produces an electrochemical redox recycling reaction inside said examination cell to produce levels of reporter that increases with time;

said program further including an analysis program for analyzing the detected level of reporter at each of said plurality of time intervals and determining the concentration of bioagent, protein or nucleic acid present in said sample when said respective bioagent, protein or nucleic acid is present in said sample and displaying said concentration on said display; and further comprising:

a magnet controlled by said electronic controller for producing a magnetic field inside said examination cell when required by said program; and means for washing the fluid in said examination cell:

said means for washing the fluid including:

first means for motivating said magnet to produce a magnetic field in said examination cell responsive to a command from said electronic controller, wherein magnetic beads in said examination cell are drawn toward said magnet leaving a portion of said examination cell vacant of magnetic beads;

second means for aspirating fluid from said bead vacated region of said examination cell when said magnetic field is present responsive to a command from said electronic controller, and third means for motivating wash fluid from said second vessel into said examination cell responsive to a command by said electronic controller following aspiration of fluid by said second means.

6. Apparatus for conducting an electrochemical enzyme linked immunosorbent assay (ELISA) for a bioagent, protein or nucleic acid comprising:

a plurality of vessels, said plurality of vessels including:

a first vessel containing 1° antibody coated magnetic beads in liquid;

a second vessel containing a wash solution;

a third vessel containing a 2° antibody linked enzyme;

a fourth vessel containing a substrate reporter; and sample holding means containing a sample solution containing said bioagent, protein or nucleic acid;

an examination cell;

an electronic controller, said electronic controller including a program, a start switch and a display;

a sensor for electrically detecting the level of reporter present in said examination cell and supplying said detected level of reporter present to said electronic controller;

said electronic controller for motivating passage of the respective contents of each of said vessels into said examination cell when required by said program and for motivating removal of the contents of said examination cell in whole or in part when required by said program;

said electronic controller including a look-up table, said look-up table containing a plurality of numbers defining slopes of lines representing detected levels of reporter versus time and a plurality of bioagent concentrations with each of said plurality of bioagent concentrations being associated with a respective one of said plurality of numbers, wherein for each slope represented in said look-up table, a concentration of said respective bioagent, protein or nucleic acid may be determined;

said program configured for performing an ELISA technique, wherein motivation of the contents of each of said vessels is motivated in a sequence to pass the contents of the respective vessels into said examination cell;

said program including means for motivating the contents of said fourth vessel into said examination cell and initiating collection of the detected level of reporter present at said sensor at each of a plurality of time intervals following motivation of the contents of said fourth vessel into said examination cell; whereby insertion of the contents of said fourth vessel into said examination cell when said respective bioagent, protein or nucleic acid is present in said examination cell produces an electrochemical redox recycling reaction inside said examination cell to produce levels of reporter that increases with time;

said program further including an analysis program for analyzing the detected level of reporter at each of said plurality of time intervals and determining the concentration of bioagent, protein or nucleic acid present in said sample when said respective bioagent, protein or nucleic acid is present in said sample and displaying said concentration on said display.

said analysis program further including:

a regression analysis program for performing a least-square linear regression analysis on said detected level of reporter taken at each of said plurality of time intervals to determine a number, said number defining a slope of a line representing detected levels of reporter versus time; and a look-up program for looking up said number determined by said regression analysis program in said look-up table and locating the corresponding concentration of said bioagent represented thereby; and further comprising;

a magnet controlled by said electronic controller for producing a magnetic field inside said examination cell when required by said program; and means for washing the fluid in said examination cell;

said means for washing including:

first means for motivating said magnet to produce a magnetic field in said examination cell responsive to a command from said electronic controller, wherein magnetic beads in said examination cell are drawn toward said magnet leaving a portion of said examination cell vacant of magnetic beads;

second means for aspirating fluid from said bead vacated region of said examination cell when said magnetic field is present responsive to a command from said electronic controller, and third means for motivating wash fluid from said second vessel into said examination cell responsive to a command by said electronic controller following aspiration of fluid by said second means.

7. The apparatus for conducting an electrochemical ELISA for a bioagent, protein or nucleic acid as defined in claim 6, wherein said means for motivating the contents of said fourth vessel into said examination cell and initiating assembly of the detected level of reporter present at each of a plurality of time intervals from said sensor further includes means for motivating said magnet to produce a magnetic field in said examination cell that extends through said sensor, wherein magnetic beads in said examination tube are drawn to said sensor.

8. The apparatus for conducting an electrochemical ELISA for a bioagent, protein or nucleic acid comprising as defined in claim 7, wherein said sensor produces an electrical current that is proportional to the quantity of reporter present in said examination cell, whereby the electrical current level increases as the amount of reporter developed with time in said examination cell increases.

9. The apparatus for conducting an electrochemical ELISA for a bioagent, protein or nucleic acid as defined in claim 8, wherein said sensor comprises a pair of spaced comb-like shaped electrodes interdigitally arranged, said spaced electrodes being located inside said examination cell to provide a current carrying path in a gap between said electrodes through at least a portion of the contents of said examination cell, and a pair of electrical conductors for respectively connecting each of said spaced electrodes to a source of potential external to said examination cell.

10. The apparatus for conducting an electrochemical ELISA for a bioagent, protein or nucleic acid as defined in claim 9, further comprising:

a plurality of electric pumps, each pump being associated with a respective one of said first through fourth vessels and said sample holding means for conveying contents from the respective vessel into said examination cell when said pump is energized;

said electronic controller being coupled to said plurality of pumps for controlling the energization of said pumps in accordance with said controller program.

11. Apparatus for conducting an electrochemical enzyme linked immunosorbent assay (ELISA) for a bioagent, protein or nucleic acid comprising:

a plurality of vessels, said plurality of vessels including:

a first vessel for holding 1° antibody coated magnetic beads in liquid;

a second vessel for holding a wash solution;

a third vessel for holding a 2° antibody linked enzyme;

a fourth vessel for holding a substrate reporter; and sample holding means for holding a sample solution containing said bioagent, protein or nucleic acid;

an examination cell;

a plurality of electric pumps, each pump being associated with a respective one of said first through fourth vessels and said sample holding means for conveying contents from the respective vessel into said examination cell when said pump is energized;

an electronic controller, said electronic controller including a program, a start switch and a display;

said electronic controller being coupled to said plurality of pumps for controlling the energization of said pumps in accordance with said controller program;

said electronic controller further including a look-up table, said look-up table containing a plurality of numbers defining slopes and a plurality of bioagent concentrations with each of said plurality of bioagent concentrations being associated with a respective one of said plurality of numbers, wherein for each slope represented in said look-up table, a concentration of said bioagent may be determined;

an aspirating pump, said aspirating pump for pumping contents from said examination cell when energized by said electronic controller;

a magnet controlled by said electronic controller for producing a magnetic field inside said examination cell when required by said program;

a sensor for electrically detecting the level of reporter present in said examination call and supplying said detected level of reporter present to said electronic controller, said sensor for producing an electrical current that is proportional to the quantity of reporter present in said examination cell;

said sensor further comprising a pair of spaced comb-like shaped electrodes interdigitally arranged, said spaced electrodes being located inside said examination cell to provide a current carrying path in a gap between said electrodes through at least a portion of the contents of said examination cell, and a pair of electrical conductors for respectively connecting each of said spaced electrodes to a source of potential external to said examination cell said electronic controller for motivating passage of the respective contents of each of said vessels into said examination cell when required by said program and for motivating removal of the contents of said examination cell in whole and/or in part when required by said program;

said program further configured for performing an ELISA technique, wherein motivation of the contents of each of said vessels is performed in a sequence to pass contents of the respective vessel into said examination cell;

means for washing the fluid in said examination cell, said means for washing further comprising:

first means for motivating said magnet to produce a magnetic field in said examination cell responsive to a command from said electronic controller, wherein magnetic beads in said examination cell are drawn toward said magnet leaving a portion of said examination cell vacant of magnetic beads;

second means for aspirating fluid from said bead vacated region of said examination cell when said magnetic field is present responsive to a command from said electronic controller, and third means for motivating wash fluid from said second vessel into said examination cell responsive to a command by said electronic controller following aspiration of fluid by said second means;

said program including means for motivating the contents of said fourth vessel into said examination cell, motivating said magnet to produce a magnetic field in said examination cell that extends through said sensor to draw magnetic beads in said examination tube to said sensor, and for obtaining from said sensor the detected level of reporter present at each of a plurality of time intervals at said sensor; whereby insertion of the contents of said fourth vessel into said examination cell when said bioagent is present in said examination cell produces an electrochemical reaction inside said examination cell to produce levels of reporter that increases with time;

said program further including an analysis program for analyzing the detected level of reporter at each of said plurality of time intervals and determining the concentration of bioagent present in said sample when said bioagent is present in said sample and displaying said concentration on said display;

said analysis program including:

a regression analysis program for performing a least-square linear regression analysis on said detected level of reporter taken at each of said plurality of time intervals to determine a number, said number defining a slope of a line representing detected levels of reporter versus time;

a look-up program for looking up said number determined by said regression analysis program in said look-up table and locating the corresponding concentration of said bioagent represented thereby.

12. Apparatus for conducting an electrochemical enzyme linked immunosorbent assay (ELISA) for a bioagent, protein or nucleic acid comprising:

an examination cell;

an electronic controller, said electronic controller including a programmed microprocessor, a start switch and a display;

a sensor for electrically detecting the level of reporter present in said examination cell and supplying said detected level of reporter present to said electronic controller;

control means, controlled by said electronic controller, for automatically producing a primary/analyte/secondary antibody with enzyme linking complex (1°Ab/analyte/2°Ab-enz complex) attached to magnetic beads and depositing said complex in said examination cell and for subsequently depositing a substrate in said examination cell;

said electronic controller for obtaining from said sensor the detected level of reporter present at said sensor at each of a plurality of time intervals; whereby insertion of said substrate into said examination cell when said bioagent, protein or nucleic acid is present in said examination cell produces an electrochemical redox recycling reaction inside said examination cell to produce levels of reporter that increases in level with the passage of time;

said electronic controller further including an analysis program for analyzing the detected level of reporter at each of said plurality of time intervals and determining the concentration of bioagent present in said sample when said bioagent, protein or nucleic a acid is present in said sample and displaying said concentration on said display.

13. The apparatus for conducting an electrochemical ELISA for a bioagent, protein or nucleic acid as defined in claim 12, wherein said substrate comprises: p-amino phenyl galactopyranoside (PAP-GP).

14. The apparatus for conducting an electrochemical ELISA for a bioagent, protein and/or nucleic acid comprising as defined in claim 12, wherein said electronic controller includes a look-up table, said look-up table containing a plurality of numbers defining slopes of lines that represent detected levels of reporter versus time and a plurality of respective bioagent, protein or nucleic acid concentrations with each of said plurality of bioagent, protein or nucleic acid concentrations being associated with a respective one of said plurality of numbers, wherein for each slope of a line represented in said took-up table, a concentration of said bioagent, protein or nucleic acid may be determined; and wherein said analysis program further comprises:
a regression analysis program for performing a least-square linear regression analysis on said detected level of reporter taken at each of said plurality of time intervals to determine a number, said number defining a slope of a line representing detected levels of reporter versus time;
a look-up program for looking up said number determined by said regression analysis program in said look-up table and locating the corresponding concentration of said bioagent represented thereby.

15. Apparatus for conducting an electrochemical ELISA for a bioagent, protein and/or nucleic acid as defined in claim 12, wherein said apparatus includes:
sample holding means for holding a sample in a solution, said sample for examination being a bioagent, protein or nucleic acid;
a second vessel for holding 1° antibody coated magnetic beads in liquid;
a third vessel for holding a 2° antibody-enzyme;
a fourth vessel for holding a wash solution;
a plurality of pumps, each of said plurality of pumps being associated with a respective one of said sample holding means and said second through fourth vessels;
a reaction cell:
a plurality of fluid conduits, each of said plurality of fluid conduits being associated with a respective one of said plurality of pumps for passing fluid pumped by an associated pump from the respective sample holding means and second through fourth vessels into said reaction cell;
a fifth vessel for holding a p-aminophenyl-glalactopyranoside (PAP-GP) in a liquid solution;
an electric two way valve, said valve having a normally closed inlet, a normally open inlet and an outlet;
an aspirating conduit coupled between said reaction cell and said normally closed inlet of said two-way valve;
a drain conduit coupled between said fifth vessel and said normally open inlet of said two-way valve;
a transfer conduit coupled between said outlet of said two-way valve and said examination cell;
a second drain conduit coupled to said examination cell;
an aspirating electric pump coupled to said second drain conduit, whereby operation of said pump produces an aspirating force in said examination cell, wherein operation of said pump when said two way valve is not energized draws fluid from said reaction cell into said examination cell and wherein operation of said pump when said two way valve is energized draws said PAP-GP from said fifth vessel into said examination cell.

16. Apparatus for conducting an electrochemical ELISA for a bioagent, protein and/or nucleic acid as defined in claim 12 wherein said apparatus includes:
sample holding means for holding a sample in a solution, said sample for examination as a bioagent;
a second vessel for holding 1° antibody coated magnetic beads in liquid;
a third vessel for holding a 2° antibody-enzyme;
a fourth vessel for holding a wash solution;
a fifth vessel for holding a p-aminophenyl-glalactopyranoside (PAP-GP) in a liquid solution;
a plurality of pumps, each of said plurality of pumps being associated with a respective one of said second through fifth vessels and said sample holding means;
a plurality of fluid conduits, each of said plurality of fluid conduits being associated with a respective one of said plurality of pumps for passing fluid pumped by an associated pump from the respective second through fifth vessels and said sample holding means into said examination cell when required by said electronic controller.

17. Apparatus for conducting an electrochemical enzyme linked immunosorbent assay (ELISA) for a bioagent, protein or nucleic acid comprising:
an examination cell;
an electronic controller, said electronic controller including a programmed microprocessor, a start switch and a display;
a sensor for electrically detecting the level of reporter present in said examination cell and supplying said detected level of reporter present to said electronic controller;
control means, controlled by said electronic controller, for automatically producing a primary/analyte/secondary antibody with enzyme linking complex (1°Ab/analyte/2°Ab-enz complex) attached to magnetic beads and depositing said complex in said examination cell and for subsequently depositing a substrate in said examination cell;
said electronic controller for obtaining from said sensor the detected level of reporter present at said sensor at each of a plurality of time intervals: whereby insertion of said substrate into said examination cell when said bioagent, protein or nucleic is present in said examination cell produces an electrochemical redox recycling reaction inside said examination cell to produce levels of reporter that increases in level with the passage of time;
said electronic controller further including an analysis program for analyzing the detected level of reporter at each of said plurality of time intervals and determining the concentration of bioagent present in said sample when said bioagent, protein or nucleic acid is present in said sample and displaying said concentration on said display; and further comprising;
a magnet controlled by said control means for producing a magnetic field inside said examination cell when required by said electronic controller; and wherein said control means includes washing means for washing the fluid in said examination cell;

said washing means including;

first means for motivating said magnet to produce a magnetic field in said examination cell responsive to a command from said electronic controller, wherein magnetic beads in said examination cell are drawn toward said magnet leaving a portion of said examination cell vacant of magnetic beads;

second means for aspirating fluid from said magnetic bead vacated portion of said examination cell when said magnetic field is present responsive to a command from said electronic controller, and third means for motivating wash fluid from said second vessel into said examination cell responsive to a command by said electronic controller following aspiration of fluid by said second means.

* * * * *